United States Patent [19]

Jekkel nee Bokany et al.

[11] Patent Number: 5,004,695

[45] Date of Patent: Apr. 2, 1991

[54] MICROBIOLOGICAL PROCESS FOR PREPARING 9α-HYDROXY-4-ANDROSTENE-3,17-DIONE

[75] Inventors: Antonia Jekkel nee Bokany; Karoly Albrecht; Gabor Ambrus; Tibor Lang; Istvan M. Szabo; Éva Ilköy; Kalman Könczöl; Imre Moravcsik; Gabor Hantos; Emilia Simonovits; Zsuzsanna Lengyel nee Szemenyei; Zsuzesanna Vida, all of Budapest; Éva Csajagi, Pécs, all of Hungary

[73] Assignee: Richter Gedeon Vegyeszeti Gyar R.T., Budapest, Hungary

[21] Appl. No.: 116,872

[22] Filed: Nov. 5, 1987

[30] Foreign Application Priority Data

Nov. 18, 1986 [HU] Hungary .......................... 4757/86

[51] Int. Cl.$^5$ .................. C12N 1/20; C12P 33/16; C12P 33/18
[52] U.S. Cl. ......................... 435/253.1; 435/55; 435/863; 435/56
[58] Field of Search ................ 435/55, 863, 54, 52, 435/53, 56

[56] References Cited

U.S. PATENT DOCUMENTS 4,035,236  7/1977  Wovcha ............................ 435/55

Primary Examiner—Elizabeth C. Weimar
Assistant Examiner—Irene Marx
Attorney, Agent, or Firm—Keil & Weinkauf

[57] ABSTRACT

The invention relates to a process for the production of 9α-hydroxy-4-androstene-3,17-dione from natural sterols of plant or animal origin or from mixtures thereof by the submerged aerobic fermentation of an enzyme-deficient, sterol-de-grading microorganism in a nutrient medium containing utilizable carbon and nitrogen sources as well as mineral salts, and by isolating the product formed, which comprises transforming the sterol or sterol mixture with the culture of a 1,2-steroid-dehydrogenase deficient strain of new Mycobacterium roseum species which is able to degrade the side-chain of natural sterols, preferably with Mycobacterium roseum sp. nov. 1108/1 deposited at the National Collection of Agricultural and Industrial Microorganisms, Budapest, Hungary under the number NCAIM B (P) 000339, and by isolating and purifying the 9α-hydroxy-4-androstene-3,17-dione obtained.

2 Claims, No Drawings

MICROBIOLOGICAL PROCESS FOR PREPARING 9α-HYDROXY-4-ANDROSTENE-3,17-DIONE

The invention relates to a new process for preparing 9α-hydroxy-4-androstene-3,17-dione by the microbial side-chain degradation of sterols of natural origin.

9α-Hydroxy-4-androstene-3,17-dione is a major starting material in the synthesis of cortico-steroid drugs [V. van Rheenen, K. P. Shepard: J. Org. Chem., 44. 1582 (1979)].

In the patent literature processes for preparing 9α-hydroxy-4-androstene-3,17-dione by microbial hydroxylation of steroids with an androstane skeleton are well known. By hydroxylating 4-androstene-3,17-dione with Nocardia spp., e.g. with *Nocardia corallina* (British Patent specification No. 862,701) and *Nocardia canicruria* (U.S. Pat. No. 4,397,947) or with *Corynebacterium equi* (Japanese Patent application No. 79-147998), 9α-hydroxy-4-androstene-3,17-dione is produced.

A *Corynespora cassiicola* fungus of the Caliciales genus hydroxylates 4-androstene-3,17-dione in the 9α-position (Japanese Patent application No. 80-77897) while *Circinella muscae* of the Mucorales genus converts testosterone to 9α-hydroxy-4-androstene-3,17-dione [P G. Rao: Indian J. Chem., 1, 314 (1963)].

Recently 9α-hydroxy-4-androstene-3,17-dione is prepared by the microbial transformation of sterols of animal or plant origin. In the patent literature this transformation is performed with the following microorganisms: *Mycobacterium fortuitum* (U.S. Pat. Nos. 4,175,006 and 4,035,236), *Mycobacterium parafortuitum* (Japanese Patent application Nos. 80-138395 and *Mycobacterium vaccae* (Japanese Patent applications Nos. 80-085397 and 82-0879).

Sterols, especially those of plant origin (β-sitosterol, campesterol), are inexpensive, easily accessible starting materials. Consequently, the production of 9α-hydroxy-4-androstene-3,17-dione by the degradation of sterols may have major economic advantage.

During industrial use the above sterol degradation processes have, however, the disadvantage of requiring prolonged fermentation periods and having relatively low production yields for 9α-hydroxy-4-androstene-3,17-dione.

During our investigations sitosterol degrading microorganisms were isolated from various soil samples according to the procedure developed by G. E. Peterson et al. [J. Lipid Research 3, 275 (1962)]. From these sterol-utilizing microorganisms a Mycobacterium strain was selected and its mutants were prepared by the mutagenic treatment of spheroplasts obtained, applying a method developed by us earlier. In the course of this process the selected strain was cultivated in a glycine and vancomycin containing medium, then the cell wall of the microorganism was lysed by lysozyme treatment and the spheroplasts and/or protoplasts obtained were treated with N-methyl-N'-nitro-N-nitroso-guanidine in a medium stabilized osmotically with saccharose. After mutagenic treatment the spheroplasts and/or protoplasts were incubated in osmotically stable solid agar medium at a temperature optimal for the growth of the bacterium for the regeneration of the cell wall.

From the regenerated bacterium colonies mutants were selected which were able to cleave the sterol side-chain and to accumulate simultaneously with high yield steroids having an androstane skeleton. Strains were selected by inoculating the above colonies into minimal agar media containing natural sterols (sitosterol, cholesterol) and 9α-hydroxy-4-androstene-3,17-dione, resp., as well as into agar media containing glycerol as carbon source. Strains showing good growth on media containing glycerol and natural sterols, resp., but failing to grow on 9α-hydroxy-4-androstene-3,17-dione-containing medium were selected.

14,000 isolates obtained by this method were screened for their ability to degrade sterols, and those which had no 1,2-steroid-dehydrogenase activity and were able to accumulate major amounts of 9α-hydroxy-4-androstene-3,17-dione by transforming natural sterols were isolated and the strain giving the highest yield of 9α-hydroxy-4-androstene-3,17-dione was selected among them. As a result of taxonomic analysis this strain differed from any known Mycobacterium spp., thus it was concluded to be a new species within its genus. The taxonomic characteristics of the new species were compared to those of the known sterol-degrading mycobacteria, see in Table 1, wherein the new strain is named *Mycobacterium roseum* sp. nov. 1108/1.

TABLE 1

Comparative taxonomical study of *Mycobacterium roseum* sp. nov. 1108/1 and known fast growing sterol-degrading Mycobacterium spp. according to selected diagnostic patterns

|  | M. roseum sp. nov. | M. phlei | M. fortuitum | M. vaccae | M. smegmatis |
|---|---|---|---|---|---|
| Pigmentation of colonies | red | orange scotochromogeneous | colourless | yellow photo- and scotochromogeneous | colourless |
| Growth at 6° C. | +++ | — | — | — | — |
| Growth on MacConkay agar | — | — | +++ | — | — |
| Thermostability at 60° C./4 hours | +++ | +++ | — | — | — |
| Tween 80 hydrolysis | +++ | +++ | varying | +++ | +++ |
| Acid formation on arabinose | — | +++ | — | ? | +++ |
| dulcitol | — | — | — | — | +++ |
| fructose | +++ | +++ | +++ | +++ | +++ |
| galactose | — | +++ | — | — | +++ |
| inositol | — | — | — | +++ | +++ |
| mannitol | — | +++ | — | +++ | +++ |
| mannose | +++ | +++ | +++ | +++ | +++ |
| sorbitol | + | +++ | — | varying | +++ |
| trehalose | +++ | +++ | +++ | +++ | +++ |
| xylose | ±; +++ | +++ | — | +++ | +++ |

*Mycobacterium roseum* sp. nov. 1108/1 is a new taxon of the Mycobacterium genus which can be differentiated on the species level. This organism, which fails to proliferate already at 45° C., can be distinctly differentiated from *Mycobacterium phlei*, active even at 52° C., utilizing citrate and succinate, forming acid on arabinose, galactose and mannitol, and producing deep yellow or orange colonies, and from *Mycobacterium smegmatis* which can well grow, similarly to *Mycobacterium phlei*, on succinate, citrate, even on oxalate and benzoate, which *Mycobacterium roseum* sp. nov. 1108/1 fails to do. Furthermore, unlike *Mycobacterium roseum* sp. nov. 1108/1, *Mycobacterium smegmatis* produces acid on nearly all diagnostic carbon sources such as arabinose, galactose, sorbitol, mannitol, inositol and fructose. *Mycobacterium smegmatis* fails to survive heat treatment at 60° C. for 4 hours and produces no pigment. *Mycobacterium roseum* sp. nov. 1108/1 can also be differentiated from *Mycobacterium fortuitum* which has always colourless colonies and fails to grow at low temperature. *Mycobacterium roseum* sp. nov. 1108/1 is a fast growing Mycobacterium with characteristic red pigmentation, it is psychrophylic (resistant to cold) and proliferates even at 6° C. in the form of mature red colonies while typical *Mycobacterium fortuitum* strains are inhibited already at 17° C. The 100 percent bright red endo-pigmentation of colonies and cultures of *Mycobacterium roseum* sp. nov. 1108/1 is of major taxonomic importance since Good (1985), investigating more than 500 *Mycobacterium fortuitum* strains, failed to find a single one with pigmentation, and so considered *Mycobacterium fortuitum* sp. to be devoid of pigmentation and non-photochromogenic.

It is an important feature of difference that *Mycobacterium fortuitum* strains exhibit good growth on Mac-Conkey agar while *Mycobacterium roseum* sp. nov. 1108/1 fails to do so even in traces. There is a distinct difference between *Mycobacterium fortuitum* strains and *Mycobacterium roseum* sp. nov. 1108/1 as regards heat resistance. Though *Mycobacterium roseum* sp. nov. 1108/1 is resistant to cold temperatures, it is also heat-resistant. Treatment at 60° C. for 4 hours is survived by the entire population. The same heat treatment completely destroys the cell mass of *Mycobacterium fortuitum*. Using xylose as carbon source which is no substrate for acid production by *Mycobacterium fortuitum* strains, *Mycobacterium roseum* sp. nov. 1108/1 is able to produce acid with temporary variability, i.e. the intensity of acid production varies between high and low for periods of several months. Finally the usually yellow photochromogenic strains of *Mycobacterium vaccae* and *Mycobacterium parafortuitum*, which are taxonomically identical according to literature sources, differ distinctly from *Mycobacterium roseum* sp. nov. 1108/1 as they are able to utilize citrate and succinate, fail to survive heat treatment at 60° C. and produce acid from inositol and mannitol.

On the basis of the above diagnostic patterns the *Mycobacterium roseum* sp. nov. 1108/1 strain is considered the representative of a new, fast growing Mycobacterium species. This strain is specified as "typical strain" and the new species is named roseum (i.e. *Mycobacterium roseum* sp. nov.). The adjective "roseum" indicates the characteristic pink to bright red colour of the species.

During the comparative taxonomic study of the new species and known Mycobacterium spp. the following literature was used: H. G. Good: Ann. Rev. Microbiol. 39, 347-69 (1985) and Bergey's Manual of Determinative Bacteriology, 8th Edition, The Williams-Wilkins Company, Baltimore, 1975.

The taxonomic features of *Mycobacterium roseum* sp. nov. 1108/1 are presented in Table 2.

TABLE 2

| Taxonomic study of *Mycobacterium roseum* sp. nov. 1108/1 | | |
|---|---|---|
| N = negative    P = positive | (P) = slightly positive | |
| Gelatin hydrolysis | N | |
| Starch hydrolysis | N | |
| Tween-40 hydrolysis | P | |
| Tween-80 hydrolysis | P | |
| Phosphatase activity | P | |
| Catalase activity | P | |
| Oxydase activity | P | |
| Urease activity | P | |
| Ammonia formation from nitrate | N | |
| Nitrite formation from nitrate | P | |
| Decomposition of adenine | P | |
| Decomposition of esculine | P | |
| Decomposition of hypoxanthine | N | |
| Decomposition of xanthine | N | |
| Tyrosine dissolution | N | |
| Utilized as sole carbon source: | | |
| Adonite | N | |
| Arabinose | N | |
| Dulcitol | N | |
| Fructose | P | |
| Galactose | N | |
| Glycerol | P | |
| Glucose | P | |
| Starch | N | |
| Inositol | N | |
| Lactose | N | |
| Maltose | N | |
| Mannitol | N | |
| Mannose | P | |
| Mucic acid | N | |
| Raffinose | N | |
| Rhamnose | N | |
| Xylose | N | |
| Calcium lactate | P | |
| Sodium acetate | N | |
| Sodium benzoate | N | |
| Sodium citrate | N | |
| Sodium gluconate | N | |
| Sodium malonate | N | |
| Sodium oxalate | N | |
| Sodium pyruvate | N | |
| Sodium salicylate | N | |
| Sodium succinate | N | |
| Utilized as sole nitrogen source: | | |
| Ammonium phosphate | P | |
| Ammonium carbonate | P | |
| Ammonium chloride | N | |
| Ammonium nitrate | P | |
| Ammonium sulfate | P | |
| Calcium nitrate | P | |
| Potassium nitrate | P | |
| Acid formation on | | |
| Adonite | P | |
| Arabinose | N | |
| Dextrine | N | |
| Dulcitol | N | |
| Fructose | P | |
| Galactose | N | |
| Glycerol | P | |
| Glucose | P | |
| Inositol | N | |
| Inuline | N | |
| Starch | N | |
| Lactose | N | |
| Mannitol | N | |
| Mannose | P | |
| Melicitose | N | |
| Raffinose | N | |

TABLE 2-continued

Taxonomic study of *Mycobacterium roseum* sp. nov. 1108/1
N = negative   P = positive   (P) = slightly positive

| | |
|---|---|
| Saccharose | P |
| Salicin | (P) |
| Sorbitol | P |
| Sorbose | N |
| Trehalose | P |
| Xylose | P (temporary variation) |
| Growth on | |
| 2% NaCl | P |
| 4% NaCl | P |
| 6% NaCl | P |
| 10% NaCl | N |
| MacConkey agar | N |
| 6° C. | P |
| Heat resistance 60° C./4 hours | P |

Based on the above, the invention relates to a process for the production of 9α-hydroxy-4-androstene-3,17-dione from natural sterols of plant or animal origin or from mixtures thereof by the submerged aerobic fermentation of an enzyme-deficient, sterol-degrading microorganism in a nutrient medium containing utilizable carbon and nitrogen sources as well as mineral salts, and by isolating the product formed, which comprises transforming the sterol or sterol mixture with the culture of a 1,2-steroid-dehydrogenase-deficient strain of the new *Mycobacterium roseum* species which is able to degrade the side-chain of natural sterols, preferably with *Mycobacterium roseum* sp. nov. 1108/1 strain deposited at the National Collection of Agricultural and Industrial Microorganisms, Budapest, Hungary under the number NCAIM B (P) 000339, and, if desired, isolating and purifying the 9α-hydroxy-4-androstene-3,17-dione obtained.

According to a preferred embodiment of the present invention the side-chain degradation is performed with *Mycobacterium roseum* sp. nov. 1108/1. The selected strain is highly advantageous due to its deficiency in 1,2-steroid-dehydrogenase activity and its fast growth. It is also a favourable feature that no expensive ingredients are required for the fermentation broth, the strain can utilize beyond nitrogen sources of natural origin (soymeal, nutmeal, corn-steep-liquor, caseine hydrolysate, yeast extract) also nitrogen of inorganic origin.

Carbon sources generally used in the fermentation industry are advantageously applied, such as glucose, fructose, saccharose, molasses, glycerol and fats. Metal ion requirement is covered by the nutritive ingredients of natural sources.

The growth of the strain is unaffected by the sterols to be transformed so the substrates may be sterilized together with the nutritive medium before inoculation.

The presence of polyoxyethylene-sorbitane monooleate (Tween-80) in the nutritive medium ensures favourable, uniform, rapid growth. Cultivation and bioconversion may be performed between 28° C. to 37° C., preferably at 32° C. The progress of transformation is monitored by thin-layer chromatography. The conversion period is short, 100 to 120 hours.

According to the experimental results 9α-hydroxy-4-androstene-3,17-dione is produced as main product by *Mycobacterium roseum* sp. nov. 1108/1 with high yields from natural sterols. In the fermentation broth minor amounts of products with partially degraded side chain are accumulated, too, namely 9α-hydroxy-3-oxo-23,24-dinor-4-cholen-22-oic acid methyl ester, 9α-hydroxy-3-oxo-23,24-dinor-4-cholen-22-oic acid, 9α-hydroxy-3-oxo-23,24-dinor-4,17(20)-choladien-22-oic acid and 9α-hydroxy-3-oxo-23,24-dinor-4,17(20)-choladien-22-aldehyde.

It is advantageous to separate the cells of the microorganism by filtration or centrifuging. The products formed during microbial conversion and adhering to the cells may be washed off with alcohols, i.e. methanol, while those in the broth may be extracted with a water immiscible solvent, such as chlorinated hydrocarbons or ethyl acetate after adjusting the pH to 2.

The main product, 9α-hydroxy-4-androstene-3,17-dione, is separated from the other products formed in minor amounts either by column chromatography or by preparative thin-layer chromatography and subsequent crystallization.

The structure of the isolated conversion products was elucidated by UV, IR, PMR and mass spectrometry.

The following examples are illustrating but not limiting the scope of the invention.

EXAMPLE 1

A cell suspension is prepared with 10 ml of sterile water from the 4 to 5 days old culture of *Mycobacterium roseum* sp. nov. 1108/1 [NCAIM B (P) 000339] grown on a potatoe-glucose agar slant. 5 ml of this suspension are used to inoculate 800 ml of sterile UFR inoculum-medium in a 3 l Erlenmeyer flask, having the following composition:

| UFR medium: | |
|---|---|
| Glycerol | 8.0 g |
| Urea | 0.4 g |
| Soymeal | 1.6 g |
| Yeast extract | 0.8 g |
| Ammonium chloride | 2.4 g |
| Calcium carbonate | 2.4 g |
| Potassium dihydrogen phosphate | 0.4 g |
| Magnesium sulfate-water 1:7 | 0.4 g |
| Ferric chloride-water 1:6 | 0.4 g |
| Tween-80 | 0.4 g |
| in 800 ml of tap water. | |

The pH of the nutritive medium is adjusted to 7 before sterilization and the mixture is sterilized at 121° C. for 45 minutes.

The flask is incubated at 32° C. for 3 days on a rotary shaker (340 rpm, diameter 3.5 cm). The contents of this flask are used to inoculate 5 l of UHF medium in a 10 l laboratory fermentor which was sterilized at 121° C. for 60 minutes.

| Composition of UHF medium: | |
|---|---|
| Glycerol | 50 g |
| Ammonium chloride | 15 g |
| Calcium carbonate | 15 g |
| Soymeal | 10 g |
| Potassium dihydrogen phosphate | 2.5 g |
| Urea | 2.5 g |
| 2:1 Mixture of β-sitosterol--campesterol | 100 g |
| Polypropylene-glycol | 30 g |
| Tween-80 | 10 g |
| Tap water ad 5 l. | |

The pH of the nutritive medium is adjusted to 7 before sterilization.

The inoculated culture is placed in a water bath at 32° C. and stirred at 350 rpm. First 90 l/h, then, with gradually diminishing foaming, 150 l/h of air flow is led through the broth.

Fermentation is continued for 120 hours, then the conversion products, formed from the mixture of β-sitosterol-campesterol, are isolated.

The sterol conversion products of one liter fermentation broth which initially contained 20 g of crude sitosterol (2:1 mixture of β-sitosterol-campesterol) are isolated as follows.

The cells of the broth are filtered, then the adhering sterol conversion products and the unchanged original materials are washed off three times with 200 ml of methanol. The pooled methanol eluates are evaporated at reduced pressure, yielding 12 g of residue.

The filtered broth is acidified with 2N sulfuric acid (pH 2). The precipitate formed, consisting of a mixture of 9α-hydroxy-3-oxo-23,24-dinor-4-cholen-22-oic acid and 9α-hydroxy-3-oxo-23,24-dinor-4,17(20)-choladien-22-oic acid, is filtered and dried for 4 hours over phosphorus pentoxide at reduced pressure. Yield: 1 g mixture of acids. The filtrate is extracted twice with 200 ml of ethyl acetate. The pooled ethyl acetate extracts are dried over anhydrous sodium sulfate, evaporated at reduced pressure, yielding 3.1 g of a residue.

The crude conversion product isolated from the cells and the residue obtained from the acidified broth by extraction are pooled and submitted to chromatography on a column consisting of 250 g of silicic acid, using n-heptane-ethyl acetate mixtures, containing gradually increasing amounts of ethyl acetate, as developing solvent. Unchanged starting material is eluated from the column with a n-heptane-ethyl acetate mixture containing 25% of ethyl acetate. On evaporating these fractions 1.5 g of a β-sitosterol-campesterol mixture is obtained. Evaporating the fractions eluted with a n-heptane-ethyl acetate mixture containing 40% of ethyl acetate and recrystallizing the residue from acetone yields 0.3 g of 9α-hydroxy-3-oxo-23,24-dinor-4-cholen-22-oic acid methyl ester, m.p. 212° to 216° C.

Evaporating the fractions eluted with a n-heptane-ethyl acetate mixture containing 45% of ethyl acetate and recrystallizing the residue from acetone 0.1 g of 9α-hydroxy-3-oxo-23,24-dinor-4,17-(20)-choladien-22-aldehyde is obtained, m.p. 204° to 209° C.

Evaporating the fractions eluted with a n-heptane-ethyl acetate mixture containing 55% of ethyl acetate at reduced pressure and recrystallizing the residue from methanol 5.7 g of 9α-hydroxy-4-androstene-3,17-dione are obtained, m.p. 219° to 221° C., $[\alpha]_D = +180°$ (c=1, chloroform).

The fractions eluted with a n-heptane-ethyl acetate mixture containing 70% of ethyl acetate are evaporated at reduced pressure, yielding a residue consisting of a mixture of 9α-hydroxy-3-oxo-23,24-dinor-4-cholen-22-oic acid and 9α-hydroxy-3-oxo-23,24-dinor-4,17(20)-choladien-22-oic acid. This mixture is pooled with the 1 g mixture of acids obtained from the filtered broth after acidification, and the entire mixture is recrystallized twice from methanol, yielding 0.4 g of chromatographically pure 9α-hydroxy-3-oxo-23,24-dinor-4,17(20)-choladien-22-oic acid, m.p. 242° to 248° C.

The mixture of 9α-hydroxy-3-oxo-23,24-dinor-4-cholen-22-oic acid and 9α-hydroxy-3-oxo-23,24-dinor-4,17(20)-choladien-22-oic acid in the recrystallizing mother liquor is separated by preparative thin-layer chromatography [adsorbent: 2:1 mixture of Kieselgel G (Reanal, Budapest) and Kieselgel 60 $HF_{254-366}$ (Reanal, Pudapest)], using a developing solvent of benzene-acetone 1:1. Yield: 0.1 g of chromatographically pure 9α-hydroxy-3-oxo-23,24-dinor-4-cholen-22-oic acid (m.p. 258° to 262° C.) and 0.2 g of 9α-hydroxy-3-oxo-23,24-dinor-4,17(20)-choladien-22-oic acid.

What we claim is:

1. A strain of the genus Mycobacterium having all of the identifying characteristics of *Mycobacterium roseum* NCAIM B (P) 000339.

2. *Mycobacterium roseum* NCAIM B (P) 000339.

* * * * *